(12) United States Patent
Xu et al.

(10) Patent No.: US 11,096,892 B2
(45) Date of Patent: Aug. 24, 2021

(54) HIGH LOADING AND FAST DISINTEGRATION FILM FOR FAST DRUG ABSORPTION

(71) Applicant: Nano and Advanced Materials Institute Limited, Hong Kong (HK)

(72) Inventors: Jinjie Xu, Hong Kong (HK); Sau Kuen Connie Kwok, Hong Kong (HK); Wah Kit Cheuk, Hong Kong (HK); Ying Li, Hong Kong (HK); Pak Ho Lau, Hong Kong (HK)

(73) Assignee: Nano and Advanced Materials Institute Limited, Hong Kong (HK)

( * ) Notice: Subject to any disclaimer, the term of this patent is extended or adjusted under 35 U.S.C. 154(b) by 20 days.

(21) Appl. No.: 16/489,351

(22) PCT Filed: Mar. 13, 2018

(86) PCT No.: PCT/CN2018/078795
§ 371 (c)(1),
(2) Date: Aug. 27, 2019

(87) PCT Pub. No.: WO2018/166432
PCT Pub. Date: Sep. 20, 2018

(65) Prior Publication Data
US 2020/0129419 A1    Apr. 30, 2020

Related U.S. Application Data

(60) Provisional application No. 62/601,099, filed on Mar. 13, 2017.

(51) Int. Cl.
*A61K 9/00* (2006.01)
*A61K 47/10* (2017.01)
*A61K 47/26* (2006.01)
*A61K 47/32* (2006.01)
*A61K 47/38* (2006.01)
*A61K 47/42* (2017.01)

(52) U.S. Cl.
CPC .............. *A61K 9/006* (2013.01); *A61K 47/10* (2013.01); *A61K 47/26* (2013.01); *A61K 47/32* (2013.01); *A61K 47/38* (2013.01); *A61K 47/42* (2013.01)

(58) Field of Classification Search
CPC ................................ A61K 9/006; A61K 9/707
See application file for complete search history.

(56) References Cited

U.S. PATENT DOCUMENTS

| 8,383,145 B2 * | 2/2013 | Asari | A61K 47/38 424/439 |
| 2005/0196440 A1 * | 9/2005 | Masters | A61K 38/38 424/464 |
| 2008/0233174 A1 * | 9/2008 | Myers | A61P 29/00 424/435 |
| 2016/0279071 A1 * | 9/2016 | Park | A61K 9/7007 |

* cited by examiner

*Primary Examiner* — Kyle A Purdy
(74) *Attorney, Agent, or Firm* — Idea Intellectual Limited; Margaret A. Burke; Sam T. Yip

(57) ABSTRACT

A film forming composition comprises a film forming component and a solvent, wherein the film forming component comprises 0-50 wt % of a first water soluble polymer, 0.3-40 wt % of a second water soluble polymer, 0-15 wt % of plasticizer and 50-70 wt % of active ingredient. The first and second water soluble polymers have a Tg of −52° C. to 216° C., and difference of Tg values of the first and second water soluble polymer is 62-268° C. The film formed by the film forming composition capable to load high content of active ingredient and lead to fast absorption of active ingredient is provided.

13 Claims, 8 Drawing Sheets

HIGH LOADING AND FAST DISINTEGRATION FILM FOR FAST DRUG ABSORPTION

CROSS-REFERENCES TO RELATED APPLICATIONS

This international application claims priority to U.S. Provisional Patent Application No. 62/601,099 filed on Mar. 13, 2017; the disclosure of which is incorporated by reference in its entirety.

FIELD OF THE INVENTION

The present invention relates generally to a film forming composition, a film product, and use of the film product.

BACKGROUND OF THE INVENTION

Of all the delivery routes, oral administration is preferred for the general population because it is easy, non-invasive and convenient. However, the conventional solid dosage forms, such as capsule or tablet, and liquid dosage forms, such as drop or syrup, have a common problem in which low oral bioavailability are observed for molecules that undergo first pass effect. Moreover, each has own drawbacks. Capsule or tablet is not preferable to users who have swallowing difficulty such as children and elders. Liquid dosage forms inherently are not preferable for unstable active ingredients. In order to overcome aforementioned issues, many pharmaceutical firms have directed their research activity in reformulating existing active pharmaceutical ingredients into rapid mouth dissolving preparations. Oral dissolving film (ODF) that readily dissolves in the oral cavity gains more attraction. This dosage form has the advantages of fast action due to quick dissolving time, ease of handling and transportation, accurate drug loading and enhanced bioavailability and good acceptance by users who have swallowing difficulty. It is well known that the major challenge of commercialized ODF is the limited drug dose that can be incorporated due to its thin form. In the current market, the highest loading in commercialized ODF is probably only 62.5 mg (produced by Novartis). However, typical doses for many therapeutic agents are over 100 mg, e.g. ibuprofen for anti-inflammatory, metoprolol tartrate for anti-hypertension and vitamin C for boosting immune system.

Typically, the thickness of conventional oral dissolving films ranges from 100-150 μm. Although thinner conventional films offer fast disintegration time, the loading of active pharmaceutical ingredient (API) in thin films is limited. Increasing the film thickness may achieve higher loading. However, the disintegration time will be increased accordingly with increasing film thickness, leading to delayed onset drug action.

Accordingly, there is a need to provide a dissolving film capable to load high content of active ingredients for fast absorption and good bioavailability.

SUMMARY OF THE INVENTION

It is the objective of the present invention to provide a film product capable to load high content of active ingredient and also quickly disintegrate for fast absorption of the active ingredient. The present film product can further load both water soluble and water insoluble active ingredients. The film product of the present invention holds 1-40 mg/cm$^2$ of active ingredient and can disintegrate within approximately 60 s. The film product of the present invention is able to load a significantly higher amount of active ingredient compare to existing dissolving film and disintegrate at a fast rate for topical (especially via buccal and/or sublingual) administration of the active ingredients. These desirable characteristics of the present film product are achieved by having a reduced amount of plasticizer and polymer, and increased thickness of the film, in contrast to conventional oral dissolving films. The present film product is porous, which, in combination with the increased thickness of the film, leads to high loading of API, yet does not slow down the dissolving time.

In accordance with one aspect of the present invention, the film forming composition comprises a film forming component and a solvent. The film forming component comprises a first water soluble polymer, a second water soluble polymer and a plasticizer. The film forming component and the solvent in the film coating composition is in a weight ratio of 1:0.5-3. Polymers suitable for the present film product should have glass temperature (Tg) of −52° C. to 261° C. In one embodiment, the difference in Tg values of the first polymer and the second polymer is 62° C.-268° C. The first and second water soluble polymer and the plasticizer together result in a film forming composition having a Tg of 20° C.-40° C. In one embodiment, the film forming composition has a Tg of room temperature. The combination of polymers of different Tg values in accordance with the present invention provides a high film tensile strength, without being brittle, and flexibility to hold a high amount of API. A water soluble polymer of Tg lower than 25° C. which exhibits high flexibility at room temperature may be used. In one embodiment, polyethylene oxide (PEO) of low molecular weight (100 k-4000 k) having a Tg lower than 25° C. is used, e.g. PEO 200 k has a Tg of −52° C. The present film forming composition includes a polymer having Tg of higher than 100° C., such as pullulan. Pullulan is a water soluble, neutral linear polysaccharide made up of α-1, 6-linked maltotriose residues. The unique linear structure of pullulan gives its high Tg and high tensile strength. In one embodiment, the pullulan suitable for the present invention has a Tg higher than 150° C., or higher than 216° C.

Plasticizer reduces inter-chain forces and increases the mobility of polymer chains to improve flexibility and extensibility of the film. This avoids chipping or cracking of the film during subsequent handling and storage. On a molecular level, plasticization of a polymer by a plasticizer leads to increased intermolecular distances (free-volume), decreased local viscosity and increased back-bone chain segmental mobility. Any biologically acceptable plasticizer may be used in the current invention, such as polyethylene glycol 400 and glycerol. Typically, the plasticizer is present in the range of ~20% by the weight of the total film product in conventional oral dissolving film. In the current invention, a reduced amount of plasticizer is used. The film forming component of the present invention comprises 0-13% by weight of plasticizer. In one embodiment, the film forming component of the present invention comprises 0-15% by weight of plasticizer. In another embodiment, the film forming component of the present invention comprises 5-8% by weight of plasticizer. In one embodiment, the film forming component of the present invention comprises 4.7-5.3% by weight of plasticizer.

The present film is useful in topical delivery of active pharmaceutical ingredient (API). Therefore, the present film product includes APIs that are administered topically. More specifically, APIs are those administered topically via buccal and/or sublingual administration. The present film can deliver hydrophilic or hydrophobic APIs. High water soluble APIs, such as metoprolol salts and vitamins, to low water soluble APIs, such as ibuprofen, may be delivered. Water soluble APIs can be readily dissolved in aqueous base polymeric solution. An API of increased solubility results in higher loading in the film. In one embodiment, the API has water solubility no less than 100 mM. While it is a challenge to incorporate high amount of a water insoluble API into an aqueous polymeric solution, the present invention separates and disperses an API in an aqueous polymeric solution at a temperature above its melting point. An API with a melting point below 100° C. may be used in the present invention. In one embodiment, the API has a melting point lower than 90° C. or lower than 80° C. In one embodiment, the film forming component comprises at least 50-70% by weight of API. The film formed from the film forming composition has 1-40 mg/cm$^2$ of API.

In accordance with second aspect of the present invention, a film is formed by the film forming composition. The film of the present invention is formed by drying the film forming composition at a desirable thickness on a surface. The film may be formed from a film applicator and a coater as commonly used in the art. Other film forming techniques may be used as appreciated by a skilled artisan. The film of the present invention is porous and has a thickness of greater than 265 μm. In one embodiment, the thickness is greater than 300 μm. In one embodiment, the thickness of the film is greater than 341 μm. The film forming composition may be dried to form a film at a temperature of 10° C.-200° C., 15° C.-150° C. or in the range of 25° C. to 100° C. The film of the present invention has a solvent content of about 5% to 10%. In one embodiment, the solvent content of the film is 5% to 8%. In another embodiment, the solvent content of the film is 6% to 7.5%. In one embodiment, the solvent content of the film is 7.16%. In an embodiment, the thickness of the film product (the dry thickness) is approximately 30%-40% of the wet film. In an embodiment, the thickness of the film product (the dry film) is 33% of the wet film.

In accordance with a third aspect of the present invention, use of a film in delivering an active ingredient topically is provided. In particular, the film product of the present invention provides an effective means to deliver high doses of an active ingredient through buccal and/or sublingual administration.

BRIEF DESCRIPTION OF THE DRAWINGS

Embodiments of the invention are described in more detail hereinafter with reference to the drawings, in which.

DETAILED DESCRIPTION OF THE INVENTION

Figure 1:
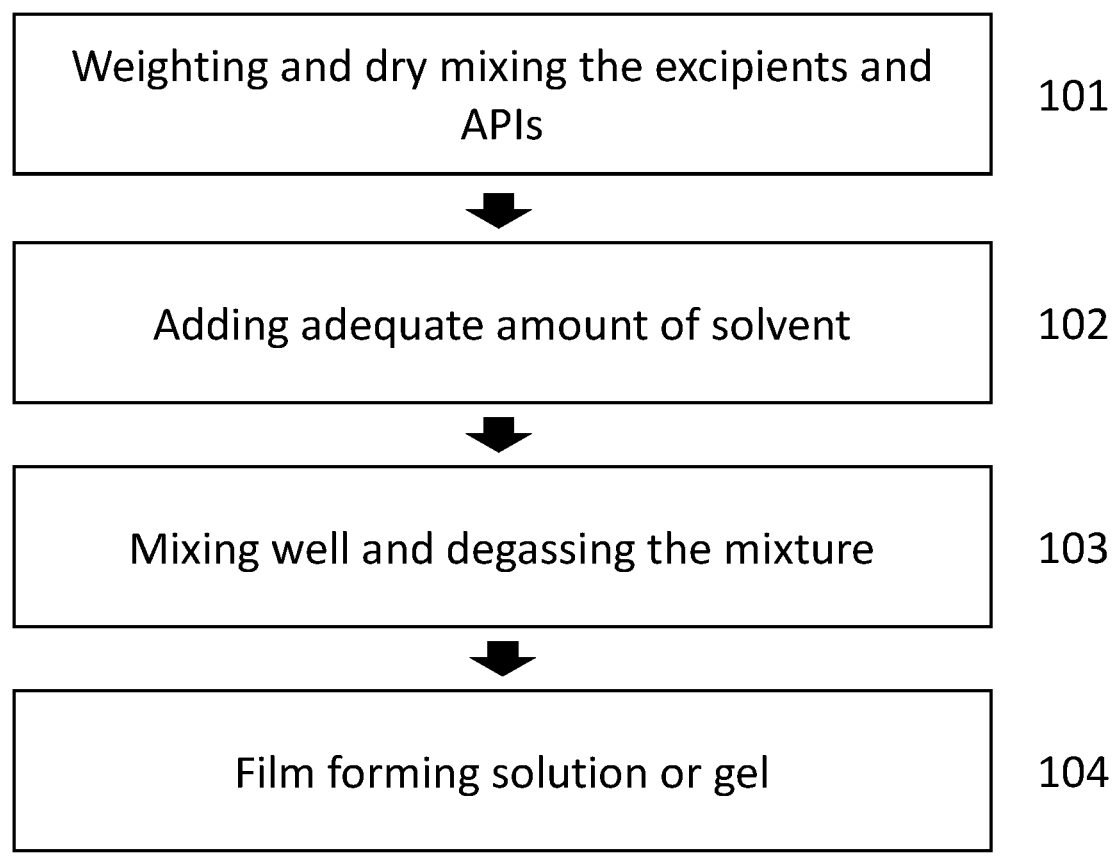
FIG. 1 depicts flow chat of preparing the film forming composition in accordance with one embodiment of the present invention.

In the following description, a film forming composition, a film product, and use of a film to topically deliver active ingredients are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation. It should be interpreted that the percentage by weight of the components of the film forming component and in the final film product is equivalent.

In accordance with one aspect of the present invention, the present invention provides a film forming composition comprises a film forming component and a solvent. The film forming component and the solvent of the film forming composition is in a weight ratio of 1:0.5-3. In one embodiment, the film forming component and the solvent of the film forming composition is in a weight ratio of 1:1.08. In another embodiment, the film forming component and the solvent of the film forming composition is in a weight ratio of 1:1.50. The solvent may be any biologically or topically compatible solvent commonly used in the art as would appreciated by a skilled person in the art, such as water and ethanol. The solvent in the film forming composition evaporates under a drying temperature. In the film product, the solvent content does not exceed 10% wt of the dry film. Examples of solvents include, but is not limited to, water and organic solvents (such as ethanol). The film forming component comprises a first water soluble polymer, a second water soluble polymer and a plasticizer. The film forming component comprises 0.3-50.1% by weight first and second water soluble polymer. In one embodiment, the film forming component comprises 0-50% by weight of the first water soluble polymer, 0.3-40% by weight of the second water soluble polymer, 0-15% by weight of the plasticizer and 50-70% by weight of active ingredient. The weight ratio of the film forming component to the solvent is 1:0.5-3. In one embodiment, the film forming component comprises 10-40% by weight of the first water soluble polymer, 0.3-10% by weight of the second water soluble polymer and 2.4-10% by weight by plasticizer. In another embodiment, the film forming component comprises 30-35% by weight of first water soluble polymer, 0.5-1% by weight of the second water soluble polymer and 2.4-5.2% by weight of plasticizer, and the film forming component has a Tg of approximately 25° C.

The first and the second water soluble polymer are different in Tg; the difference between the Tg values of the two water soluble polymers is 62-268° C. In one embodiment, the first polymer has a glass transition temperature (Tg) of 126° C.-216° C., a second polymer has a Tg of −52° C.-64° C. The first polymer has a higher Tg than the second polymer. The first and second water soluble polymer and the plasticizer together result in a film forming component having Tg of 20° C.-40° C. In one embodiment, the film forming component has a Tg of room temperature. In yet another embodiment, the film forming component has a Tg of approximately 25° C. The combination of polymers of different Tg values results in a film to have sufficient tensile strength, without being brittle, and flexibility to hold a high amount of API. In one embodiment, the ratio of water soluble polymer of higher Tg (first water soluble polymer) to water soluble polymer of lower Tg (second water soluble polymer) is 1:16 to approximately 2:1. In one embodiment, the ratio of water soluble polymer of higher Tg (first water soluble polymer) to water soluble polymer of lower Tg (second water soluble polymer) is 0~1:10. In one embodiment, the ratio of water soluble polymer of high Tg (first water soluble polymer) to water soluble polymer of lower Tg (second water soluble polymer) is 43:1. In one embodiment, the ratio of water soluble polymer of high Tg (first water soluble polymer) to water soluble polymer of lower Tg (second water soluble polymer) is 34-35:1. Water soluble polymers with Tg lower than 25° C. which exhibit high flexibility at room temperature may be used in the present invention. In one embodiment, polyethylene oxide (PEO) of low molecular weight (100 k-4000 k) having a Tg lower than 25° C. is used. In particular, PEO 200 k having a Tg of −52° C. may be used. In one embodiment, the polymer having a Tg of higher than 100° C. may be pullulan. Pullulan is a water soluble, neutral linear polysaccharide made up of α-1, 6-linked maltotriose residues. The unique linear structure of pullulan gives it its high Tg and high tensile strength. In one embodiment, the pullulan suitable for the present invention as a Tg higher than 150° C., or higher than 216° C. Water soluble polymers suitable for the film forming component of the present invention include, but are not limited to, pullulan, hydroxypropyl methylcellulose, hydroxypropyl cellulose, polyethylene oxide and polyvinylpyrrolide.

A film formed by the film forming composition in accordance with the present invention can hold 1-40 mg/cm$^2$ of an active pharmaceutical ingredient (API). In some embodiments, a density of 17.97 mg/cm$^2$ of active ingredient can be held in the present film product. In some embodiments, the film product holds 14.37 mg/cm$^2$ of active ingredient. In one embodiment, the active ingredient is at least 45-70% by weight of the film or the film forming component. Such high loading of the active ingredient of the present film product is achieved by the low percentage of plasticizer and polymer, and increased thickness of the film which increases the porosity and space within the film to hold more of the active ingredient. The combination of polymers of different Tg values also give the film sufficient tensile strength to hold the high content of API, yet flexible without being brittle. Conventional dissolving films contain ~20% by weight of plasticizer. In one embodiment, the film forming component of the present invention comprises 0-15% by weight of plasticizer. In one embodiment, the film forming component of the present invention comprises 4.5-10.1% or 4.5-7.5% by weight of plasticizer. In one embodiment, the film forming component of the present invention comprises 4.5-6.3% by weight of plasticizer. In one embodiment, the film forming component of the present invention comprises 4.7-5.3% by weight of plasticizer. Plasticizers readily used in the art that are biologically compatible are applicable in the present invention. Examples of plasticizers include, but are not limited to, dextran, PEG 400, glycerol and sorbitol.

In one embodiment, the film forming composition further comprises an active ingredient. The active ingredient or API herein referred to herein, is a compound, molecule or substance that is biologically active for pharmaceutical or medical applications. The active ingredient can be hydrophobic or hydrophilic. In particular, the active ingredient may be one that is orally administered. In one embodiment, the active ingredient is buccally or sublingually administered. Water soluble or hydrophilic active ingredients are both readily dissolved in the aqueous based polymers of the present film product. In one embodiment, the active ingredient has a water solubility of no less than 100 mM. The film in accordance with the present invention may be formed by drying the film forming composition at a drying temperature of 10° C.-200° C., 15° C.-150° C. or in the range of 25° C. to 100° C. When water insoluble or hydrophobic active ingredient has a melting point lower than the drying temperature, these water insoluble active ingredients are separated and dispersed in the aqueous based polymer film. As a result, an aqueous based polymer film with a high loading of evenly contributed hydrophilic or hydrophobic active ingredient is formed. Any active ingredient with a melting point below 200° C. is suitable for the present invention. In one embodiment, the API having a melting point lower than 150° C., lower than 100° C., lower than 90° C. or lower than 80° C. is suitable for the present invention. In one embodiment, API having a melting point lower than 70° C. is suitable for the present invention. Examples of APIs suitable for the present invention include, but are not limited to, ibuprofen, metoprolol tartrate and vitamin C. In one embodiment, the film forming component comprises at least 45-70% by weight of API. The film formed from the film forming composition has 1-40 mg/cm$^2$ of API.

In one embodiment, the film forming composition further comprises a filler, disintegrating agent, flavor, sweetener, surfactant or antifoaming agent or a combination thereof. Examples of fillers include, but are not limited to, starch, modified starch, and silk fibroin. Examples of disintegrating agents include, but are not limited to, sodium starch glycolate and hydroxypropyl beta cyclodextrin. An exemplary sweetener may be trehalose. Surfactants and antifoaming agents commonly used in the art may be used in the present invention, such as tween 20 and simethicone.

Figure 2:
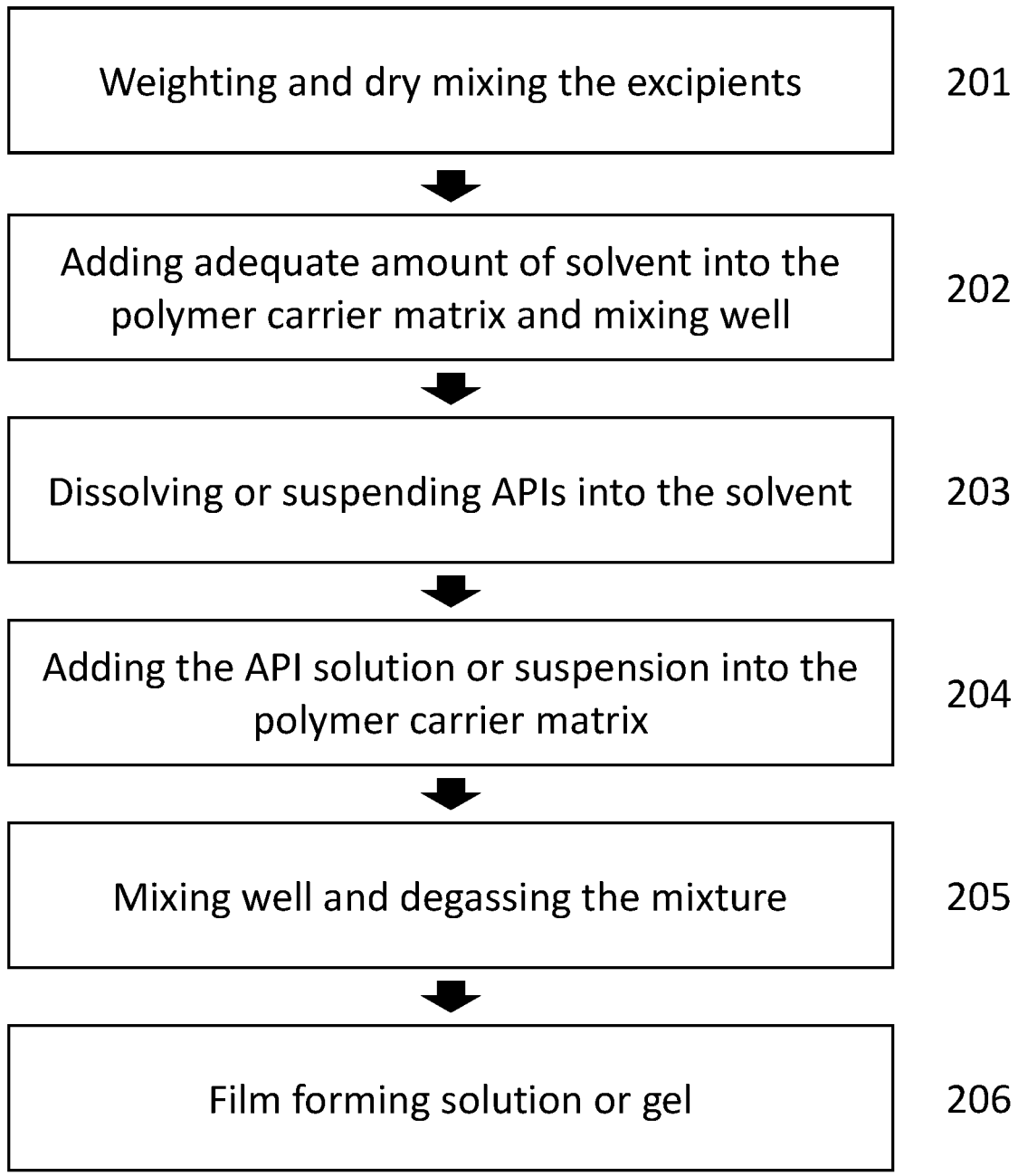
FIG. 2 depicts flow chat of preparing the film forming composition in accordance with one embodiment of the present invention.
Figure 3:
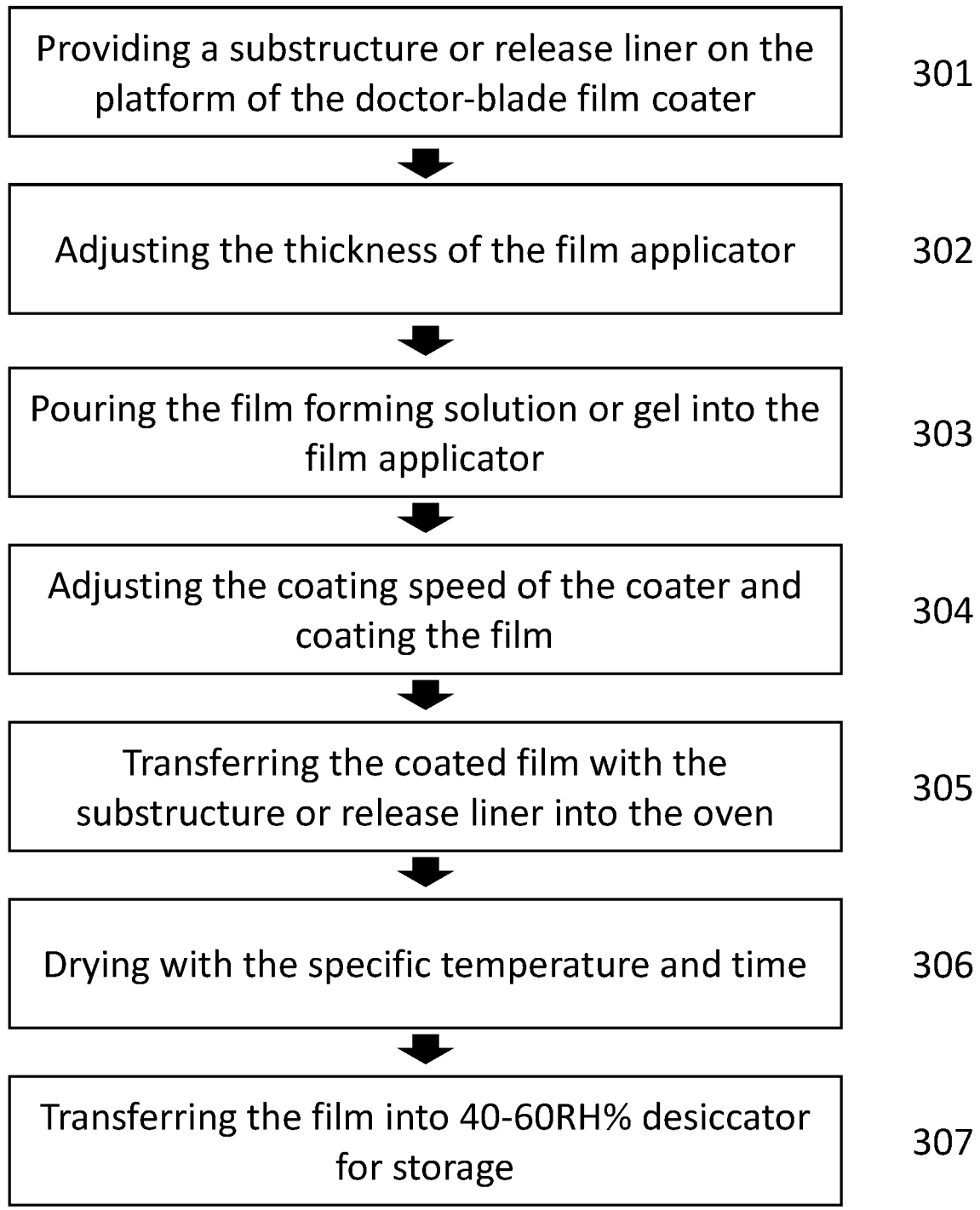
FIG. 3 depicts flow chat of preparing the film in accordance with one embodiment of the present invention.

In a second aspect of the present invention, the present invention provides a film formed by the film forming composition. The film may be formed by coating, overlaying, painting, depositing the film forming composition on a surface and drying the film forming composition. In one embodiment, a wet film of approximately 1000 µm thickness of film forming composition is deposited. The wet film herein referred to as a layer of film forming composition before drying to form the film product. The film formed from the film forming composition or the dry film has a thickness of 30%-40% of the wet film. In an embodiment, the thickness of the film product (the dry film) is 33% of the wet film. The film of the present invention has a solvent content of about 5% to 10%. In one embodiment, the solvent content of the film is 5% to 8%. In another embodiment, the solvent content of the film is 6% to 7.5%. In one embodiment, the solvent content of the film is 7.16%. FIGS. 1-3 describes the steps of preparing a film and a film forming composition in accordance with the present invention. In FIG. 1, step 101, all excipients (the film forming component excluding the API including, but not limited to, water-soluble polymers, fillers, plasticizers, disintegrating agents, sweeteners, surfactants and antifoaming agents) and hydrophilic or hydrophobic APIs are weighed and mixed to get a homogenous mixture in the solid phase. In step 102, solvents including water and/or a polar organic solvent or any combination thereof is added to the solid mixture. In step 103, the mixture is mixed with overhead stirrer for a sufficient time period and speed as required as would appreciated by a skilled in the art. The degas process is performed with a Thinky cream mixer or centrifuge under a non-vacuum mixing environment. The degas process can be omitted if the mixing environment is performed in a vacuum environment. The type of the mixing machine is not restricted to the above-mentioned mixers in the presently claimed invention. Any appropriate mixing equipment may be applicable in the present invention. At 104, the film forming solution or gel-like solution is formed in 104. FIG. 2 is a flowchart illustrating steps of method for preparing a film forming solution or gel-like solution including hydrophilic and hydrophobic APIs for high loading and fast dissolving film for oral administration according to another embodiment of the presently claimed invention. In step 201, all excipients including, but are not limited to, water-soluble polymers, fillers, plasticizers, disintegrating agents, sweeteners, surfactants and antifoaming agents are weighted and mixed to get a homogenous mixture in solid phase. In step 202, an adequate amount of solvents, including water and/or a polar/non-polar organic solvent or any combination thereof, is added to the solid mixture. In step 203, the hydrophilic or hydrophobic APIs are dissolved or suspended into the solvent, including water and/or a polar/non-polar organic solvent or any combination thereof. In step 204, the API containing film forming solution or gel-like solution is added into the polymer carrier matrix which formed in the step 202. In step 205, the mixture of step 204 is mixed with an overhead stirrer. The type of the mixing machine is not restricted to the mentioned mixers in the presently claimed invention. Any appropriate equipment may be applicable and covered by present invention. After Step 205, the film forming solution or gel-like solution is formed in 206. Degassing step may be omitted if mixing step is performed under vacuum environment. FIG. 3 is a flowchart illustrating steps of a film casting method for high loading and fast dissolving film for oral administration according to an embodiment of the presently claimed invention. In step 301, a substructure or release liner is provided and put on a platform of a doctor-blade film coater. In step 302, the thickness of the film applicator is adjusted to a thickness corresponding to the desire thickness of the film. Thickness of the film is determined by thickness of the gap of the film applicator. The film of the present invention is in range of 265-360 µm. In step 303, the film forming solution or gel-like solution is poured into the film applicator. In step 304, the coating speed is adjusted to a specific speed and the film is coated. In step 305, the coated film with the substructure or release liner is transferred into oven. In step 306, the film is dried. In step 307, the film is transferred into 40-60% relative humidity (RH) desiccator for storage. Drying temperature in step 306 should be selected. A low drying temperature leads to extremely long drying process resulting in high manufacturing cost. Increasing temperature could shorten drying process. However, the drying temperature should not exceed the decomposition temperatures of the materials in the film so that all the materials could maintain their intact molecular structures. In one embodiment of the present invention, it is desirably to have the drying temperature no more than 200° C. More desirably, the drying temperature is no more than 150° C., or no more than 100° C. The film may be formed by coating the film forming composition at a desirable thickness on a flat surface and allowing it to dry.

Figure 5:
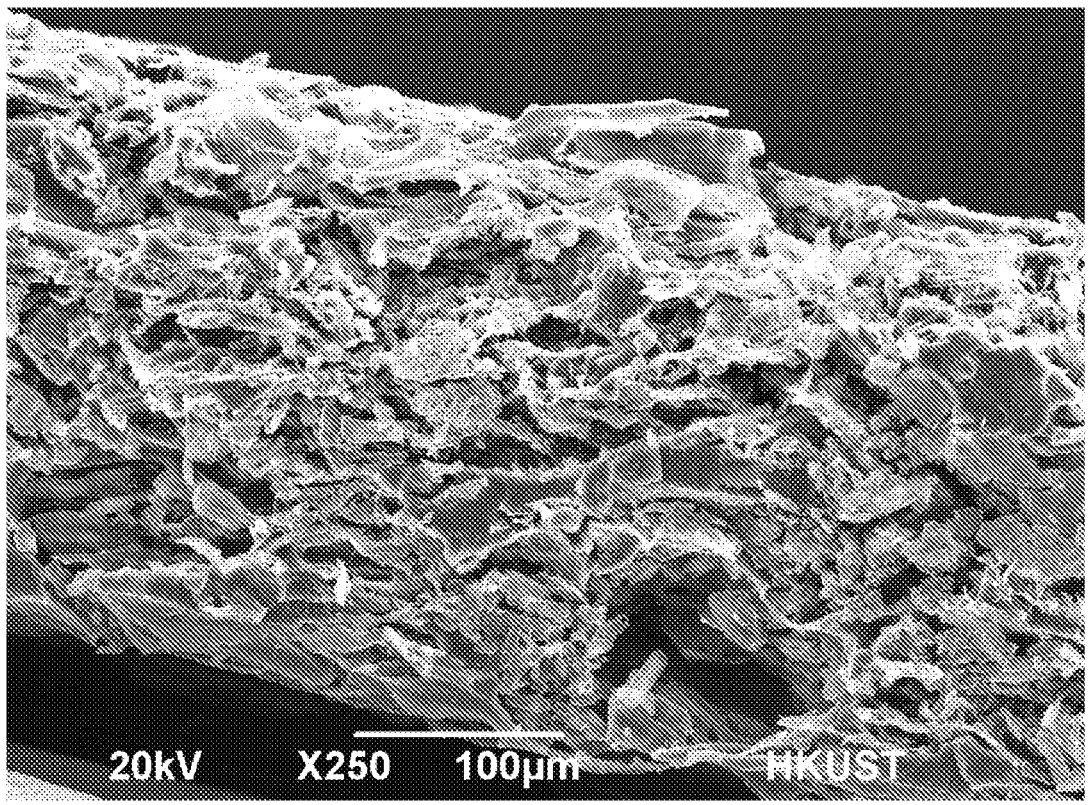
FIG. 5 depicts microscopic image of the film of one embodiment of the present invention.
Figure 6:
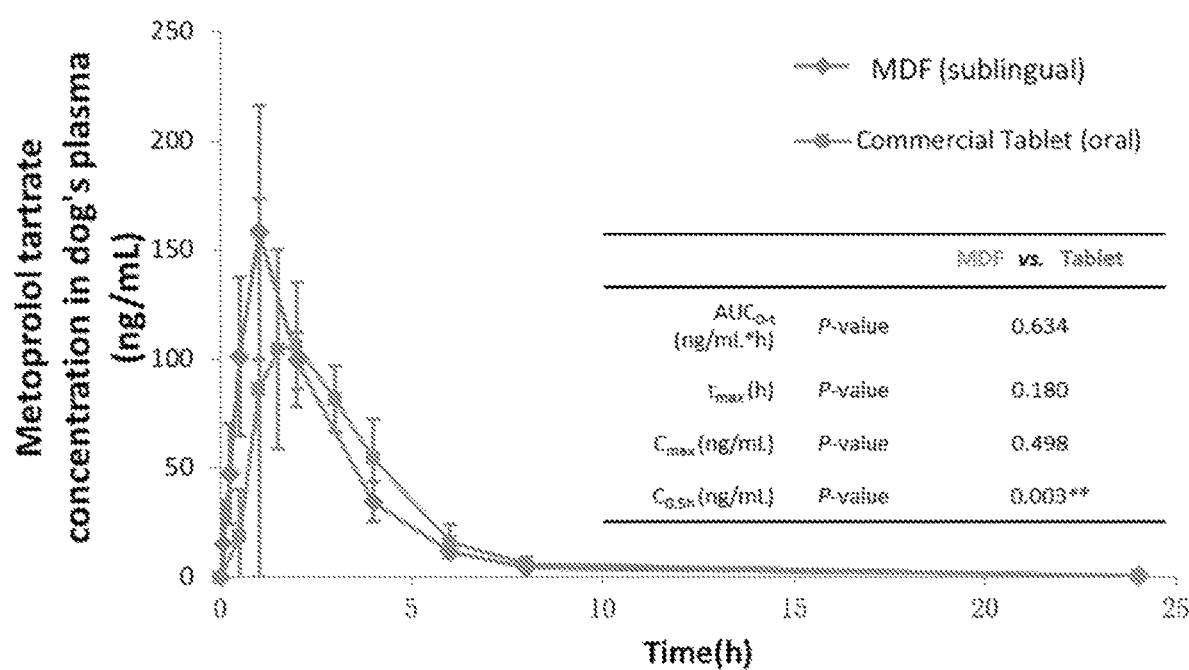
FIG. 6 depicts water soluble active ingredient absorption rate of film in accordance to one embodiment of the present invention and commercial oral tablet.
Figure 7:
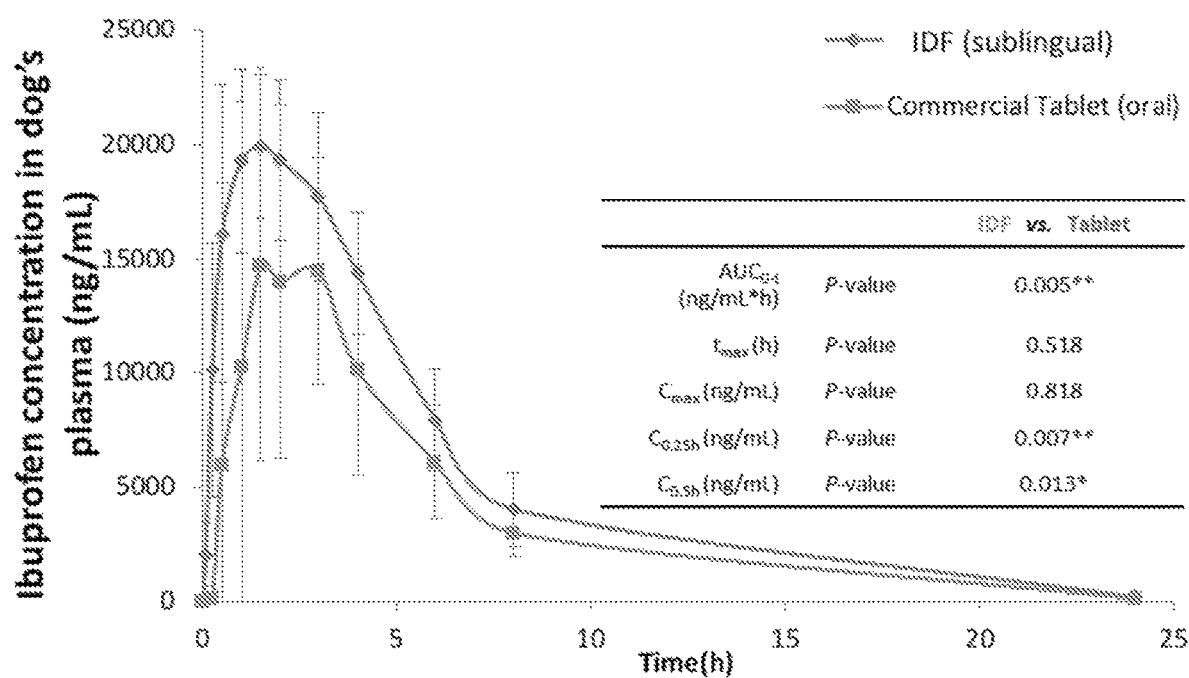
FIG. 7 depicts water insoluble active ingredient absorption rate of film in accordance to one embodiment of the present invention and commercial oral tablet.

Conventional dissolving films generally have thicknesses of 100-150 µm with a disintegration time of approximately 60 s. In the present invention, the films may range from 265-360 µm. In one embodiment, the film has a thickness of greater than 265 µm and a disintegration time of approximately 47 s. In one embodiment, the inventive film has a thickness of greater than 341 µm and a disintegration time of approximately 57 s. The highly porous structure of the films of the present invention (FIGS. 4 and 5) maintains the fast disintegration time for fast absorption despite the increased thickness of the film. In accordance with the present invention, the film comprises 0.3%-50.1% by weight of water soluble polymer, 0-15% of plasticizer and 45-70% by weight of active ingredient and a water content of no more than 10%. The film of the present invention has a water content of about 5% to 10%. In one embodiment, the water content of the film is 5% to 8%. In another embodiment, the water content of the film is 6% to 7.5%. In one embodiment, the water content of the film is 7.16%. The film of the present invention has sufficient tensile strength to hold 1-40 mg/cm$^2$ of active ingredient, and flexible without being brittle. The film of the present invention disintegrates within approximately 10 s to 300 s for fast delivery and absorption of active ingredient. In one embodiment, the film of the present invention disintegrates in approximately 40 s-60 s. FIG. 6 illustrates the pharmacokinetic profiles of metoprolol tartrate in a beagle dog via sublingual administration of the present film formulation (metoprolol tartrate dissolving film, MDF) against a commercial oral tablet. It is shown that at 0.5 h after administration, metoprolol tartrate plasma concentration of the present film is significantly higher than the commercial tablet (t test: P-value <0.01**). This demonstrates that absorption of the active ingredient through the present film is faster than the commercial form. Similar fast absorption of the active ingredient is demonstrated in FIG. 7. FIG. 7 shows plasma concentration of ibuprofen via sublingual administration of the present film (ibuprofen dissolving film, IDF) vs. a commercial oral tablet. At 0.25 h and 0.5 h after administration, the ibuprofen plasma concentration is much higher via the sublingual administration of the present film. Furthermore, the present film is demonstrated to provide higher bioavailability of the active ingredient as seen by the significant higher $AUC_{0-t}$ than commercial oral tablet.

In accordance with a third aspect of the present invention, the present invention provides use of a film product of the present invention in delivering active ingredient orally. In particular, the film product of the present invention provides an effective means in delivering the active ingredient through buccal and/or sublingual administration. In one embodiment, the method of orally delivering active ingredient comprises providing a film having a thickness of at least 265 µm comprising 0-51.1% a first water soluble polymer, 0.3-40% a second water soluble polymer, 0-15% plasticizer by weight and no more than 10% water content to an area of buccal cavity of a subject. In one embodiment, the film is administered under the tongue of the subject.

The description of the present invention has been provided for the purposes of illustration and description. It is not intended to be exhaustive or to limit the invention to the precise forms disclosed. The embodiments were chosen and described in order to best explain the principles of the invention and its practical application, thereby enabling others skilled in the art to understand the invention for various embodiments and with various modifications that are suited to the particular use contemplated.

One skilled in the art would readily appreciate that different functions discussed herein may be performed in a different order and/or concurrently with each other. Many modifications and variations will be apparent to the practitioner skilled in the art. Furthermore, if desired, one or more of the embodiments described herein may be optional or may be combined. Other aspects and advantages of the present invention will be apparent to those skilled in the art from a review of the present application.

EXAMPLES

Example 1

Different film forming compositions accordance with the present invention are shown in Table 1. The ratio of the two water soluble polymers is investigated.

TABLE 1

Ibuprofen containing film composition of the present invention

| | IDF | | | | | | | | | |
|---|---|---|---|---|---|---|---|---|---|---|
| | 3 | 4 | 5 | 6 | 7 | 9 | 10 | 11 | 12 | 16 |
| Ibuprofen | 50.0% | 50.0% | 50.0% | 50.0% | 47.6% | 50.0% | 50.0% | 50.0% | 50.0% | 50.0% |
| HPMC (E15) | 8.0% | 4.5% | 2.4% | 26.7% | 25.3% | 24.0% | 24.0% | 20.0% | 20.0% | 24.0% |
| PEO (200K) | 32.0% | 35.5% | 37.6% | 13.3% | 12.7% | 12.0% | 12.0% | 10.0% | 10.0% | 12.0% |
| Potato starch | 5.0% | 5.0% | 5.0% | 5.0% | 4.8% | 9.0% | — | 15.0% | — | 4.5% |
| Simethicone | 5.0% | 5.0% | 5.0% | 5.0% | 4.8% | 5.0% | 5.0% | 5.0% | 5.0% | 5.0% |
| Dextran 70 | — | — | — | — | 4.8% | — | 9.0% | — | 15.0% | 4.5% |
| PEO (600K) | — | — | — | — | — | — | — | — | — | — |
| Solution Characterization: | | | | | | | | | | |
| Bending | | | | 3 | 3 | 3 | 3 | N/A | 3 | 3 |
| Tensile strength (kPa) | | | | N/A | 3.03 | N/A | 3.44 | N/A | N/A | N/A |
| Peeling | | can't form a film | | 3 | 3 | 2 | 2 | 0 | 1 | 2 |
| Disintegration time (second) | | | | >300 | 40 | 240 | 180 | 120 | 180 | 225 |

The Ibuprofen dissolving formulations (IDF) 7 is prepared as follows: 1.07 g hydroxypropyl methylcellulose (E15), 0.53 g polyethylene oxide (M.W. 200K), 0.20 g potato starch, 0.20 g Dextran 70, 0.20 g simethicone and 2.00 g ibuprofen are weighted into a weighing cup. The weighing cup is then placed under an overhead stirrer, stirred with 100 rpm for 10 min to obtain a homogenous powder mixture. 4 ml ethanol is added into the powder mixture, stir with 1000 rpm for 10 min in 70° C. water bath. 3 ml of DI water is added into the mixture and stirred for 10 min with 1000 rpm until a homogenous gel A is formed in 70° C. water bath. The homogenous white gel A is then transferred into a 24 mL cream container and degassed with a Thinky cream mixer at 400 rpm for 4 mins to remove large bubbles inside the gel. The gel A is ready for film casting. A PET release liner is placed on the platform of the—blade film coater. The film applicator is adjusted to the thickness of 500 µm for film coating. The gel A is poured into the coater and coated with the coating speed of 8 mm/s. The formed film is placed into 70° C. oven for 1 hour than transferred into desiccator with 40-60% RH for storage. IDF 3-6, 9-12 and 16 are also prepared in the same way as described above.

Table 1 illustrates IDF in accordance with the present invention. The film forming compositions of Table 1 vary in ratio of the first and second water soluble polymers. Table 1 shows that ratio the water soluble polymer of higher Tg (e.g. HPMC) to the water soluble polymer of lower Tg (e.g. PEO 200K) is 1:15 to 2:1 in order to form a film to hold 50% by weight of active ingredient. In an embodiment, the percentage by weight of the water soluble polymer of lower Tg is 37.6% or less of the film forming component excluding the active ingredient. In one embodiment, the percentage by weight of the water soluble polymer of higher Tg is approximately 2.4% or higher of the film forming component. In one embodiment, a high tensile strength of over 3 kPa is achieved in the presence of silk fibroin.

Example 2

Table 2 shows IDF 27, 29-37 in accordance with the present invention.

TABLE 2

Ibuprofen containing film composition of the present invention

| | IDF | | | | | | | | | |
|---|---|---|---|---|---|---|---|---|---|---|
| | 27 | 29 | 30 | 31 | 32 | 33 | 34 | 35 | 36 | 37 |
| Ibuprofen | 50.0% | 50.0% | 50.0% | 50.0% | 50.0% | 50.0% | 50.0% | 50.0% | 60.0% | 50.0% |
| PEO (200K) | 24.0% | 24.0% | 24.0% | 24.0% | 24.0% | 24.0% | 26.6% | 24.0% | 24.0% | 24.0% |
| PEO (600K) | 6.0% | 6.0% | 6.0% | 6.0% | 3.0% | — | — | 6.0% | 6.0% | 6.0% |
| Simethicone | 5.0% | 5.0% | 5.0% | 5.0% | 5.0% | 5.0% | 5.0% | 5.0% | 5.0% | 5.0% |
| Potato starch | 15.0% | 7.5% | 7.5% | 7.5% | 15.0% | 15.0% | 15.0% | — | — | — |
| Dextran 70 | — | 7.5% | — | — | — | — | — | — | — | — |
| Maltodextrin (16.5-19.5) | — | — | 7.5% | — | — | — | — | — | — | — |
| D-sorbitol | — | — | — | 7.5% | — | — | — | — | — | — |
| HPMC (E15) | — | — | — | — | 3.0% | — | — | — | — | — |
| PEO (4,000K) | — | — | — | — | — | 6.0% | 3.4% | — | — | — |
| PVP | — | — | — | — | — | — | — | 15.0% | 5.0% | 7.5% |

TABLE 2-continued

Ibuprofen containing film composition of the present invention

| | IDF | | | | | | | | | |
|---|---|---|---|---|---|---|---|---|---|---|
| | 27 | 29 | 30 | 31 | 32 | 33 | 34 | 35 | 36 | 37 |
| PEG 400 | — | — | — | — | — | — | — | — | — | 7.5% |
| Solution Characterization: | | | | film forming component:Ethanol:Water = 4:5:3 | | | | | | |
| Bending | 3 | 3 | 3 | 3 | 3 | 3 | 3 | 3 | 3 | 3 |
| Tensile strength (kPa) | 0.75 | 0.45 | 0.55 | 0.69 | 0.58 | 0.36 | 0.47 | 0.58 | 0.66 | 0.44 |
| Peeling | 3 | 3 | 3 | 3 | 3 | 3 | 3 | 3 | 3 | 3 |
| Disintegration time (second) | 130 | 151 | 147 | 143 | 173 | 200 | 93 | 228 | 238 | 262 |

IDF 27-37 are film forming compositions in accordance with the present invention. Tensile strength of the film is increased by reducing the amount of water soluble polymer of higher Tg value.

IDF34 is prepared as follows: 2.13 g polyethylene oxide (M.W. 200K), 1.20 g potato starch and 0.27 g polyethylene oxide (M.W. 4,000K) are weighted into a weighing cup. The weighing cup is then placed under an overhead stirrer, stirred with 100 rpm for 10 min to obtain a homogenous powder mixture. 0.40 g Simethicone is weighted and added into the powder mixture and mixed for 10 min with 100 rpm. 6 ml of DI water is added into the mixture and stirred for 10 min with 3000 rpm until a homogenous gel A is formed. 4.00 g Ibuprofen is weighted and dissolved into 10 mL Ethanol with 1000 rpm stirring for 5 minutes at 70° C. water bath and named ibuprofen solution. Ibuprofen solution s added into gel A and stirred for 15 min with 3000 rpm at 70° C. water bath until a homogenous translucent gel B s formed. The homogenous white gel B s transferred into a 50 mL falcon tube and centrifuged at 4000 rpm for 15 second to remove large bubbles inside the gel. The gel B is ready for film casting. A Loparex PET release liner is placed on the platform of the doctor-blade film coater. The film applicator is adjusted to the thickness of 1200 μm for film coating. The gel B is poured into the coater and coated with the coating speed of 4 mm/s. The formed film is placed into 70° C. oven for 1 hour than transferred into desiccator with 40-60% RH for storage. IDF 27-33 and 35-37 are also prepared in the same way as described above.

Example 3

Table 3 shows IDF 56-61, 65, 67 and 69 in accordance with the present invention.

TABLE 3

Ibuprofen containing film composition of the present invention

| | IDF | | | | | | | | |
|---|---|---|---|---|---|---|---|---|---|
| | 56 | 57 | 58 | 59 | 60 | 61 | 65 | 67 | 69 |
| Ibuprofen | 50.0% | 50.0% | 50.0% | 50.0% | 50.0% | 50.0% | 50.0% | 52.6% | 51.3% |
| Pullulan | 48.8% | 36.6% | 36.6% | 36.6% | 13.0% | 36.6% | 36.6% | 31.6% | 34.1% |
| HPC (100K) | 1.3% | 0.9% | 0.9% | 0.9% | — | 0.9% | 0.9% | — | 0.5% |
| Trehalose | — | 12.5% | 6.3% | — | — | — | 11.3% | — | 5.8% |
| PEG 400 | — | — | 6.3% | — | — | — | — | — | — |
| Sodium starch glycolate | — | — | — | 12.5% | 10.0% | — | 1.3% | 7.4% | 4.2% |
| PEO (200K) | — | — | — | — | 0.3% | — | — | 2.1% | 1.0% |
| Modified starch | — | — | — | — | 26.7% | 12.5% | — | — | — |
| Glycerol | — | — | — | — | — | — | — | 4.2% | 2.1% |
| Tween20 | — | — | — | — | — | — | — | 1.6% | 0.8% |
| D-sorbitol | — | — | — | — | — | — | — | 0.5% | 0.3% |
| Solution Characterization: | | | | film forming component:Water = 4:6 | | | | | |
| Bending | 3 | 3 | 3 | 3 | 0 | 3 | 3 | 3 | 2 |
| Tensile strength (kPa) | 1.57 | 1.25 | 0.58 | 0.6 | N/A | 0.91 | 1.96 | 0.25 | 1.01 |
| Peeling | 3 | 3 | 3 | 3 | 3 | 3 | 3 | 3 | 3 |
| Disintegration time (second) | 278 | 76 | 49 | 45 | 15 | 223 | 140 | 26 | 57 |

IDF 56-61, 65, 67 and 69 are film forming composition in accordance with the present invention. These compositions include highly water soluble filler (e.g trehalose) and disintegration agent (e.g. sodium starch glycolate) and liquid phase polymer (PEG400). Combination of polymers, fillers and disintegration agents increases solubility of the film and/or leads to a film of reduced density with more space for faster disintegration and having the mechanical strength to hold high loading of active ingredient.

IDF69 is prepared as follows: 2.66 g Pullulan, 0.04 g Hydroxypropyl cellulose (M.W. 100K), 0.08 g polyethylene oxide (M.W. 200K), 0.45 g Trehalose, 0.02 g D-sorbitol, 0.33 g Sodium starch glycolate and 4.00 g Ibuprofen are weighted into a weighing cup. The weighing cup is then placed under an overhead stirrer, stirred with 100 rpm for 10 min to obtain a homogenous powder mixture. 0.16 g glycerol and 0.06 g Tween 20 are weighted and added into the powder mixture and mixed for 10 min with 100 rpm. 12 ml of DI water is added into the mixture and stirred for 20 min with 3000 rpm until a homogenous white gel A was formed. The whole mixing process is under room temperature and condition. The homogenous white gel A is transferred into a 50 mL falcon tube and centrifuged at 4000 rpm for 60 second to remove large bubbles inside the gel. The gel A is ready for film casting. A Loparex PET release liner is placed on the platform of the doctor-blade film coater. The film applicator is adjusted to the thickness of 1000 μm for film coating. The gel A is poured into the coater and coated with the coating speed of 4 mm/s. The formed film is placed into 70° C. oven for 1 hour than transferred into desiccator with 55-60% RH for storage. IDF 56-61, 65, 67 are also prepared in the same way as described above.

Example 4

Table 4 shows film forming compositions in accordance with the present invention.

TABLE 4

Metoprolol tartrate containing film composition of the present invention

| | MDF | | | | | | |
|---|---|---|---|---|---|---|---|
| | 5 | 17 | 19 | 22 | 25 | 29 | 32 |
| Metoprolol tartrate | 59.8% | 55.4% | 58.1% | 53.6% | 54.8% | 53.6% | 54.1% |
| Pullulan | 28.1% | 31.1% | 27.3% | 30.2% | 30.8% | 30.2% | 30.4% |
| PEO (200K) | 0.8% | 0.9% | 0.8% | 0.9% | 0.9% | 0.9% | 0.9% |
| D-sorbitol | 0.5% | 0.6% | 0.5% | 0.5% | 0.5% | 0.5% | 0.5% |
| Glycerol | 4.3% | 4.7% | 4.2% | 4.6% | 4.7% | 4.6% | 4.7% |
| Tween20 | 1.5% | 1.7% | 1.5% | 1.6% | 1.6% | 1.6% | 1.6% |
| Simethicone | 5.0% | 5.5% | 4.9% | 5.4% | 5.5% | 5.4% | 5.4% |
| Beta cyclodextrin | — | — | 2.9% | 3.2% | 1.1% | 1.1% | 1.1% |
| Silk fibroin | — | — | — | — | — | 2.1% | 1.3% |
| Solution (film forming component: water) | 1:1 | 10:9 | 1:1 | 10:9 | 10:9 | 10:9 | 10:9 |
| Characterization: | | | | | | | |
| Bending | 3 | 3 | 3 | 3 | 3 | 3 | 3 |
| Tensile strength (kPa) | 0.93 | 1.1 | N/A | N/A | 0.31 | 1.46 | 1.06 |
| Peeling | 3 | 3 | 3 | 3 | 3 | 3 | 3 |
| Disintegration time (second) | 42 | 41 | N/A | N/A | N/A | N/A | 47 |

Metoprolol tartrate film forming composition (MDF) 5, 17, 19, 22, 25, 29 and 32 are shown in Table 4. Table 4 illustrates film forming composition of fixed ratio of the two water soluble polymers.

MDF 32 is prepared as follows: 2.81 g Pullulan, 0.08 g polyethylene oxide (M.W. 200K), 0.05 g D-sorbitol, 0.10 g (2-Hydroxypropyl)-β-cyclodextrin and 0.12 g Silk fibroin are weighted into a weighing cup. The weighing cup is then placed under an overhead stirrer, stirred with 100 rpm for 10 min to obtain a homogenous powder mixture. 0.43 g glycerol and 0.15 g Tween 20 are weighted and added into the powder mixture and mixed for and other 10 min with 100 rpm. 5.00 g Metoprolol tartrate is weighted and dissolved into 10 mL DI water with 1000 rpm stirring for 5 minutes and named Metoprolol tartrate solution. Metoprolol tartrate solution is added into the mixture and stirred for 20 min with 3000 rpm until a homogenous translucent gel A is formed. The whole mixing process is performed under room temperature and condition. The homogenous white gel A is then transferred into a 24 mL cream container and degassed with a Thinky cream mixer at 400 rpm for 4 mins to remove large bubbles inside the gel. The gel A is ready for film casting. A Loparex PET release liner is placed on the platform of the doctor-blade film coater. The film applicator is adjusted to the thickness of 800 μm for film coating. The gel A is poured into the coater and coated with the coating speed of 8 mm/s. The formed film is placed into 100° C. oven for 40 minutes than transferred into desiccator with 40-60% RH for storage. MDF 5, 17, 19, 22, 25 and 29 are also prepared as described above.

Example 5

Table 5 shows vitamin C film forming composition (VDF) in accordance with the present invention

TABLE 5

Vitamin C containing film forming composition of the present invention

| | VDF | | | | | | | |
|---|---|---|---|---|---|---|---|---|
| | 1 | 2 | 3 | 4 | 5 | 6 | 7 | 8 |
| Vitamin C | 65.0% | 65.0% | 65.0% | 8.0% | 29.9% | 30.0% | 15.0% | 31.2% |
| Pullulan | 28.2% | 28.2% | 28.2% | 8.4% | 49.5% | 47.5% | 47.5% | 49.3% |
| Glycerol | 4.0% | 4.0% | 4.0% | 2.5% | 7.0% | 8.7% | 8.7% | 9.0% |
| D-sorbitol | 0.5% | 0.5% | 0.5% | 2.5% | 0.9% | 1.1% | 1.1% | 1.1% |
| Tween 20 | 1.5% | 1.5% | 1.5% | 5.0% | 2.6% | 2.6% | 2.6% | 2.7% |
| PEG 400 | 0.8% | — | — | — | — | — | — | — |
| PEO (1,000K) | — | 0.8% | — | — | — | — | — | — |
| PEO (200K) | — | — | 0.8% | — | 1.4% | 1.4% | 1.4% | 1.4% |
| PVP (K90) | — | — | — | 5.0% | — | — | — | — |
| Hydroxypropyl beta dextrin | — | — | — | 33.6% | — | — | — | — |
| Sodium alginate | — | — | — | 15.0% | — | — | — | — |
| sodium chloride | — | — | — | 20.0% | — | — | — | — |
| Simethicone | — | — | — | — | 8.7% | 8.8% | 8.8% | 5.2% |
| H.A. (200 KDa) | — | — | — | — | — | — | 15.0% | — |
| Solution (film forming component: water) | 1:1 | 1:1 | 1:1 | 1:1.2 | 1:1.2 | 1:1.2 | 1:2.4 | 1:1.3 |
| Characterization: | | | | | | | | |
| Banding | 1 | 1 | 3 | 1 | 3 | 3 | 3 | 3 |
| Peeling | 3 | 3 | 3 | 3 | 3 | 3 | 3 | 1 |
| Disintegration time (second) | 30 | 30 | 20 | 10 | 10 | 20 | 30 | 10 |

VDF 1-8 are film forming composition in accordance with the present invention. Percentage by weight of pullulan is fixed to 8.4%-49.5%. Disintegration time is shortened by increasing amount of water soluble polymer, including a high solubility polymer (e.g. pullulan) and/or including disintegrating agent (e.g. beta-cyclodextrin). An increased amount of water soluble polymer and/or polymer of higher solubility shorten disintegration time. As seen in VDF3 and VDF5, a 20% increase of pullulan shorten the disintegration time by half. Addition of beta-cyclodextrin in VDF-4 keeps the disintegration time short with a low content of highly soluble polymer. Disintegration time is significantly reduced.

VDF 5 is prepared as follows: 4.97 g pullulan, 0.15 g polyethylene oxide (M.W. 200K), 0.09 g D-sorbitol, 0.7 g glycerol, 0.26 g tween20, 0.88 g simethicone and 3.00 g vitamin C are weighted into a weighing cup. The weighing cup is then placed under an overhead stirrer, stirred with 100 rpm for 10 min to obtain a homogenous powder mixture. 12 ml of DI water is added into the mixture and stirred for 20 min with 3000 rpm until a homogenous gel A is formed. The homogenous white gel A is transferred into a 50 mL falcon tube and degassed with 4400 rpm centrifuge for 60 s to remove the large bubbles inside the gel. The gel A is ready for film casting. A PET release liner is placed on the platform of the doctor-blade film coater. The film applicator is adjusted to the thickness of 300 μm for film coating. The gel A is poured into the coater and coated with the coating speed of 8 mm/s. The formed film is placed into 70° C. oven for 1 hour than transferred into desiccator with 40-60% RH for storage. VDF 1-4, 6-8 are prepared in the same way as described above.

Film formed from the film forming compositions in above Examples 1-5 are characterized based on the following:

Bending

Films of the presently claimed invention are tested for bending. The film is bended 90° towards the right side and bended 90° towards the left side. A complete bending cycle is counted 90° to left then 90° to right. The score of the bending test is set as 3 equals to bend 30 cycles or above, 2 equals to 20-29 cycles, 1 equals to 10-19 cycles and 0 equals to less than 9 cycles. Bending test reflects the flexibility of the film which is an important parameter during the film fabrication in large scale. The factors that affected the film flexibility are the film thickness, polymer carrier matrix hardness and coherence, moisture percentage and defect inside the film. As seen in Tables 1-5, film of the present invention remains highly flexible with at least 50% of API loading.

Peeling

Peeling is the estimation of the ease that the film can be removed from the substructure. Peeling property also related to the surface tension, adhesiveness and polymer coherence of the film. The score of the peeling is depended on how easy the film can be removed from the substructure. The score of 3 equals to very easy to remove and without any significant effort for removing the film. 2 equals to easy but with little effort to remove the film. 1 equals to can be removed but need to apply more effort. 0 equals to unable to be removed from the substructure. As seen from Tables 1-5, films of the present invention are easily remove from a substructure. Therefore, film products according to the present invention can be easily transferred from one surface to another.

Disintegration

The term disintegration referred herein does not imply a complete dissolution or breakdown of the film or the active ingredient contained therein. The term disintegration referred herein is defined as a state the film starts to break up by visual inspection.

TABLE 6

Disintegration time of commercial dissolving film and films of the present invention

|  | Disintegration time (second) | | | Batch to Batch | | |
| --- | --- | --- | --- | --- | --- | --- |
|  | Average (s): | SD: | % RSD: | Average (s): | SD: | % RSD: |
| commercial set 1 | 47.17 | 1.94 | 4.11% | 50.89 | 3.40 | 6.68% |
| commercial set 2 | 51.67 | 3.98 | 7.71% |  |  |  |
| commercial set 3 | 53.83 | 2.93 | 5.44% |  |  |  |
| IDF69C27RT Batch 1 | 55.67 | 2.52 | 4.52% | 57.22 | 1.68 | 2.93% |
| IDF69C27RT Batch 2 | 57.00 | 5.00 | 8.77% |  |  |  |
| IDF69C27RT Batch 3 | 59.00 | 4.58 | 7.77% |  |  |  |
| MDF32C21 Batch 1 | 51.00 | 3.61 | 7.07% | 47.22 | 3.40 | 6.68% |
| MDF32C21 Batch 2 | 46.33 | 1.53 | 3.30% |  |  |  |
| MDF32C21 Batch 3 | 44.33 | 4.04 | 9.12% |  |  |  |

Figure 8:
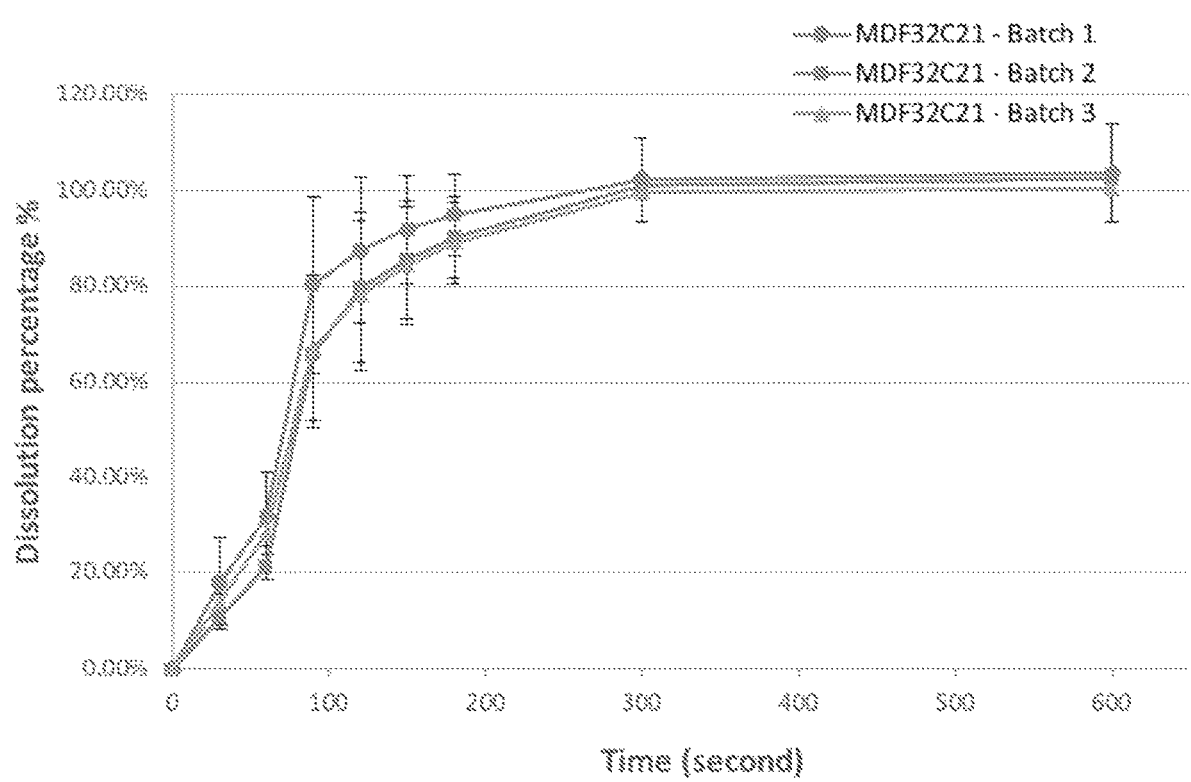
FIG. 8 depicts rate of dissolution of metoprolol tartrate from a film in accordance to one embodiment of the present invention.

Table 6 shows the disintegration time of a commercial dissolving film (GasX for gas relieve in GI tract), IDF69 and MDF32 film of the present invention. Each dissolving film is tested for 3 times under USP 701 disintegration test. All of the samples are disintegrated within a minute and MDF 32 has the shortest disintegration time. The average disintegration time for three different batch samples is 47 s for MDF 32, 51 s for commercial product and 57 s for IDF 69. Disintegration time of the film of the present invention is comparable to commercial dissolving film. Dissolution indicates the amount of active ingredient in the film turns into solution per unit time. FIG. 8 shows dissolution percentage of MDF32 over time. It is demonstrated that active ingredient in the film of the present invention turns into solution completely within approximately 300 sec.

Tensile Strength

Tensile strength of the film is measured according to the ASTM D 882-02 Standard test method for tensile properties of thin plastic sheeting with Texture analyser. This test method determines tensile properties of the plastics in the form of thin sheeting, including film, the thickness of the specification is less than 1 mm thick. The test specimen is required to have uniform width (range 5-25.4 mm) and thickness (<1 mm). The test is modified according to Kumar et al. International journal of innovative drug discovery, 4, 46-53, 2014, oral film study to fulfil the size of the present invention. The samples size is 2.2 cm×3.7 cm, grip separation of the texture analyser is 20 mm; crosshead speed is 1 inch/min throughout the tensile test.

The calculation of the tensile strength: Tensile strength=Force at break (N)/Cross-sectional area (mm$^2$)

TABLE 7

Tensile strength of a commercial dissolving film and films of the present invention

|  |  |  |  | Batch to Batch | | |
| --- | --- | --- | --- | --- | --- | --- |
|  | Average (kPa): | SD: | % RSD: | Average (kPa): | SD: | % RSD: |
| commercial set 1 | 1.04 | 0.06 | 5.76% | 1.11 | 0.06 | 5.74% |
| commercial set 2 | 1.12 | 0.06 | 5.68% |  |  |  |
| commercial set 3 | 1.17 | 0.03 | 2.20% |  |  |  |
| IDF69C27RT-Batch 1 | 0.96 | 0.17 | 17.66% | 1.01 | 0.06 | 5.48% |
| IDF69C27RT-Batch 2 | 1.01 | 0.08 | 8.17% |  |  |  |

TABLE 7-continued

Tensile strength of a commercial
dissolving film and films of the present invention

|  | Average (kPa): | SD: | % RSD: | Batch to Batch Average (kPa): | SD | % RSD: |
|---|---|---|---|---|---|---|
| IDF69C27RT-Batch 3 | 1.07 | 0.07 | 6.65% | | | |
| MDF32C21-Batch 1 | 0.95 | 0.03 | 3.32% | 1.06 | 0.14 | 12.88% |
| MDF32C21-Batch 2 | 1.01 | 0.11 | 10.39% | | | |
| MDF32C21-Batch 3 | 1.21 | 0.08 | 6.33% | | | |

Table 7 shows tensile strength of a commercial dissolving film (GasX), IDF 69 and MDF 32 of the present invention. Each film is tested for three times. Average tensile strength for IDF 69 is 1.01, MDF is 1.06 and commercial dissolving film is 1.11. It is shown that the film of the present invention has tensile strength comparable to commercial dissolving film.

Loading

To determine the API amount in the film, HPLC analysis is developed to detect the API concentration in the film for different APIs. And by analysing the API concentration, it can help to monitor and control the formulation and the fabrication process with the accurate amount of APIs inside the film. There are two possible ways to increase the API amount of a fixed size film. One is to increase the film thickness and another one is to increase the percentage of the API in the film matrix. For increasing the API percentage in film, the challenge is that each polymer matrix has an upper limit for holding a specific amount of loose or crystallized APIs. This can only be modified by changing to suitable polymer and other excipients to increase the amount of API holding in the film. For increasing the film thickness to increase the API amount in the film, the increased film thickness will eventually increase the disintegration time of the film as well, and cannot develop a fast dissolving film, and therefore the thickness of the film should be studied. In the present invention, the film is able to load a high concentration of API without increasing the disintegration time of the film, while maintaining fast absorption of the active ingredient.

TABLE 8

API concentration of the films of the present invention

|  | Average (mg/cm$^2$): | SD: | % RSD | Batch to Batch Average (mg/cm$^2$): | SD | % RSD |
|---|---|---|---|---|---|---|
| IDF69C27RT Batch 1 | 15.51 | 1.1 | 7.06% | 14.37 | 0.99 | 6.91% |
| IDF69C27RT Batch 2 | 13.74 | 0.15 | 1.12% | | | |
| IDF69C27RT Batch 3 | 13.86 | 0.08 | 0.56% | | | |
| MDF32C21 Batch 1 | 18.37 | 1.12 | 6.10% | 17.97 | 0.48 | 2.70% |
| MDF32C21 Batch 2 | 17.43 | 1.3 | 7.44% | | | |
| MDF32C21 Batch 3 | 18.1 | 1.21 | 6.67% | | | |

Table 8 above shows API concentration of films of the present invention. A commercial dissolving film is typically a 2.2 cm×3.7 cm oral strip. Therefore, it is shown that dissolving film of the present invention can load over 100 mg of API in a 2.2 cm×3.7 cm strip.

Thickness

The dry film thickness is affected by the wet film thickness which is controlled by the film applicator and also the solid content percentage of the film forming solution or gel. The thickness is proportional API amount, however at the same time, it is also proportional to the disintegration time of the film. And hence, increasing the film thickness will increase the API amount and disintegration time of the film. Therefore, the film thickness and composition is optimized in this presently claimed invention to obtain a good thickness film to have high loading and fast disintegating.

TABLE 9

Wet and dry thickness of the film of the present invention

|  | Wet thickness (μm): | Dry thickness (μm): | Wet to dry percentage: | Average (μm): | SD | % RSD |
|---|---|---|---|---|---|---|
| IDF69C27RT Batch 1 | 1000 | 337 | 33.7% | 341.4 | 3.87 | 1.1% |
| IDF69C27RT Batch 2 | 1000 | 342 | 34.2% | | | |
| IDF69C27RT Batch 3 | 1000 | 345 | 34.5% | | | |
| MDF32C21 Batch 1 | 800 | 266 | 33.2% | 266.6 | 3.07 | 1.2% |
| MDF32C21 Batch 2 | 800 | 270 | 33.8% | | | |
| MDF32C21 Batch 3 | 800 | 264 | 33.0% | | | |

Table 9 shows the wet and dry thickness of the film of the present invention. It is shown that the wet to dry percentage of the present film is approximately 30-35%.

Appearance

Figure 4:
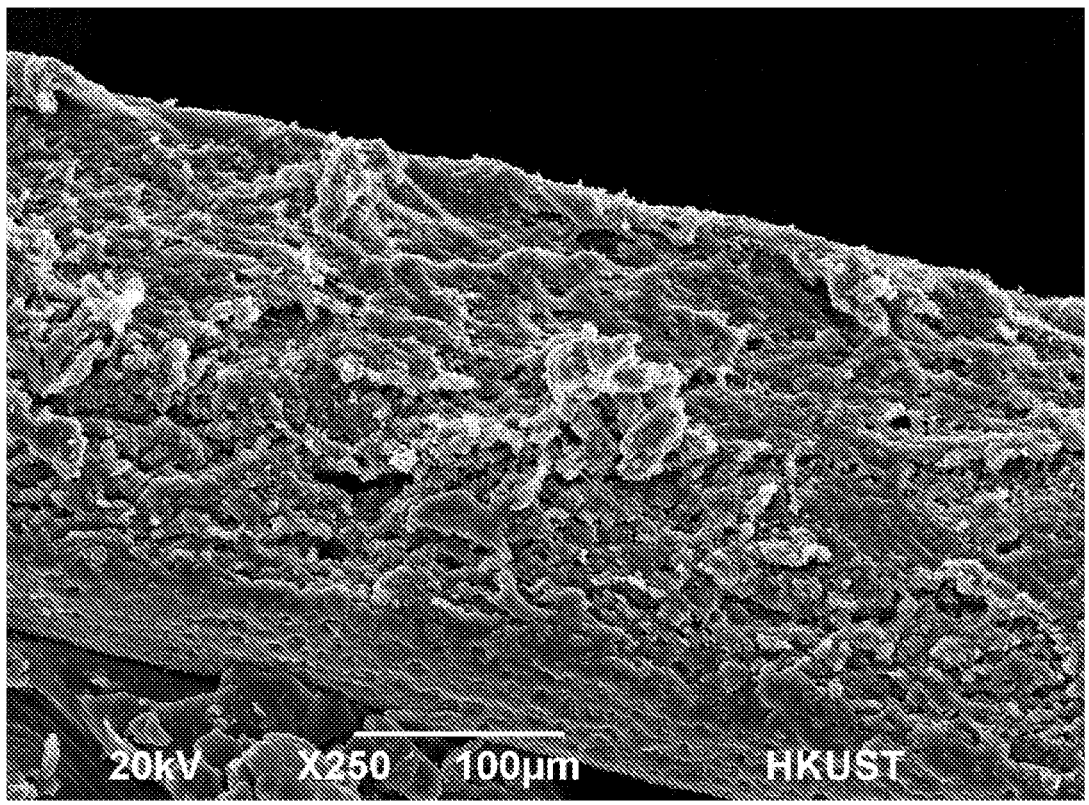
FIG. 4 depicts microscopic image of the film of one embodiment of the present invention.

The appearance of the film is affected by the drying time and temperature as well as the film forming component. APIs' crystallinity is also a factor to affect the film formation and, as a result, change the morphology of the surface. FIG. 4 is the cross-sectional image of MDF32 under scanning electronic microscope. The particles of the polymer carrier matrix and API are clearly observed. The particles are mainly in tiny granule with uniform size distribution of less than several micrometres and closely packed together. Tiny pores are clearly observed on the surface of the sample. These tiny pores help to rapidly absorb the water and shorten the film disintegration time. FIG. 5 is the cross-sectional image of IDF 69 under scanning electronic microscope. The particles in the figure are irregular shape and size. The surface of the sample is full of cracks and voids. The particles appear as flake-like form with the size of tens micrometre and structure as layer by layer formation. Spaces and voids are found inside the cross-section of the film. These defects are favourable for fast disintegration however weaken the mechanical strength of the film at the same time.

Example 6

Animal study is performed to investigate the pharmacokinetic of water soluble active ingredient in the film of the present invention. Table 10 is summary of the pharmacokinetic study of metoprolol oral dissolving film of the present invention and commercial metoprolol oral tablet in Beagle dogs.

TABLE 10

Pharmacokinetic animal study of water soluble active ingredient

| Group | Dosage forms | Animal No. | Dosage (mg) | Administration |
|---|---|---|---|---|
| Group 1 (Sublingual) | oral dissolving film | 1-6 | 25 mg | The oral dissolving films are affixed to the lower part under the tongue, and closed its mouth for 5 min |
| Group 2 (p.o.) | Tablet | 1-6 | 25 mg | The dogs are orally administered tablets |

Two forms of metoprolol (oral tablet and oral dissolving film of the present invention) are administered to the same six Beagle dogs (with 6 days washout period). For Group 1, blood samples are collected into EDTA. 2K tubes from the fore leg vein of dogs before dosing and at 0.083, 0.25, 0.5, 1, 2, 4, 6, 8, 24 h after dosing. For Group 2, blood samples are collected at 0.5, 1, 2, 3, 4, 6, 8, 24 h. The plasma samples are separated through centrifuge immediately and stored at −80° C. until analysis. The concentration of metoprolol in plasma samples are determined by LC-MS/MS. The pharmacokinetic parameters of different administration ways are calculated by DAS 3.2.8 and statistically analyzed by SPSS 17. Each group is performed for 3 times. Tables 11 and 12 show the plasma concentration of metoprolol in group 1 and group 2, respectively. The average plasma concentration-time curve is shown in FIG. 6. The pharmacokinetic study shows the dissolving film of the present invention exhibits a faster absorption and high bioavailability of water soluble active ingredient than the commercial readily use oral administered tablet.

TABLE 11

Plasma concentration of group 1

| Time (h) | Plasma concentration of metoprolol (ng/mL) | | | | | | | |
|---|---|---|---|---|---|---|---|---|
| | Dog1 | Dog2 | Dog3 | Dog4 | Dog5 | Dog6 | Mean | SD |
| 0 | 0 | 0 | 0 | 0 | 0 | 0 | 0 | 0 |
| 0.083 | 9.5 | 54.3 | 7.9 | 4.8 | 9.2 | 9.3 | 15.8 | 18.9 |
| 0.25 | 29.9 | 82.2 | 41.5 | 21.5 | 43.1 | 67.7 | 47.7 | 23 |
| 0.5 | 54.8 | 77.1 | 112 | 107 | 94.1 | 162 | 101.2 | 36.4 |
| 1 | 88.9 | 257 | 123 | 135 | 166 | 180 | 158.3 | 58.1 |
| 2 | 110 | 89.4 | 77.3 | 107 | 104 | 109 | 99.5 | 13.2 |
| 4 | 45.8 | 39.1 | 19.9 | 34.6 | 38.3 | 29.5 | 34.5 | 9 |
| 6 | 16.6 | 10.9 | 6.9 | 10.9 | 12.6 | 11.3 | 11.5 | 3.1 |
| 8 | 7.4 | 4.1 | 2.8 | 3.6 | 5.2 | 4.1 | 4.5 | 1.6 |
| 24 | 0.5 | 0.5 | 0.3 | 0.3 | 0.3 | 0.3 | 0.4 | 0.1 |

TABLE 12

Plasma concentration of group 2

| Time (h) | Plasma concentration of metoprolol (ng/mL) | | | | | | | |
|---|---|---|---|---|---|---|---|---|
| | Dog1 | Dog2 | Dog3 | Dog4 | Dog5 | Dog6 | Mean | SD |
| 0 | 0 | 0 | 0 | 0 | 0 | 0 | 0 | 0 |
| 0.5 | 0.6 | 49.9 | 1.5 | 23.5 | 2.2 | 35.9 | 18.9 | 20.9 |
| 1 | 44.5 | 137 | 31.6 | 52.9 | 12.4 | 240 | 86.4 | 86.6 |
| 1.5 | 153 | 132 | 86.9 | 101 | 23.9 | 129 | 104.3 | 45.9 |
| 2 | 143 | 107 | 98.9 | 126 | 58.9 | 105 | 106.5 | 28.4 |
| 3 | 101 | 60.5 | 71.1 | 78.9 | 94.5 | 85.6 | 81.9 | 15 |
| 4 | 66.2 | 36.7 | 48.7 | 46.8 | 85.6 | 41.2 | 54.2 | 18.4 |
| 6 | 24 | 11.7 | 11.2 | 13.1 | 28.1 | 10.7 | 16.5 | 7.6 |
| 8 | 10.8 | 4.3 | 4.6 | 4.4 | 9.6 | 4.4 | 6.3 | 3 |
| 24 | 0.4 | 0.3 | 0.2 | 0.3 | 0.2 | 0.1 | 0.3 | 0.1 |

Example 7

Animal study is performed to investigate the pharmacokinetic parameters of water insoluble active ingredient in the film of the present invention. Table 13 is summary of the pharmacokinetic study of ibuprofen oral dissolving film of the present invention and commercial ibuprofen oral tablet in Beagle dogs.

TABLE 13

Pharmacokinetic animal study of water insoluble active ingredient

| Group | Dosage forms | Animal No. | Dosage (mg) | Administration |
|---|---|---|---|---|
| Group 1 (Sublingual) | oral dissolving film | 1-6 | 60 mg | The oral dissolving films are affixed to the lower part under the tongue, and close its mouth for 5 min |
| Group 2 (p.o.) | Tablet | 1-6 | 60 mg | The dogs are orally administered tablets |

Two forms of ibuprofen (oral tablet and oral dissolving film of the present invention) are administered to the six Beagle dogs (with 6 days washout period). For Group 1, blood samples are collected into EDTA. 2K tubes from the fore leg vein of dogs before dosing and at 0.083, 0.25, 0.5, 1, 1.5, 2, 3, 4, 6, 8, 24 h after dosing. For Group 2, blood samples are collected at 0.25, 0.5, 1, 1.5, 2, 3, 4, 6, 8, 24 h. The plasma samples are separated through centrifuge immediately and stored at −80° C. until analysis. The concentration of metoprolol in plasma samples are determined by LC-MS/MS. The pharmacokinetic parameters of different administration ways are calculated by DAS 3.2.8 and statistically analyzed by SPSS 17. Each group is performed for 2 times. Tables 14 and 15 show the plasma concentration of ibuprofen in group 1 and group 2, respectively. The average plasma concentration-time curve is shown in FIG. 7. The pharmacokinetic study shows the dissolving film of the present invention exhibits a faster absorption and high bioavailability of water insoluble active ingredient than the commercial readily use oral administered tablet.

TABLE 14

Plasma concentration of Group 1

| Time (h) | Plasma concentration of Ibuprofen (ng/mL) | | | | | | | |
|---|---|---|---|---|---|---|---|---|
| | Dog1 | Dog2 | Dog3 | Dog4 | Dog5 | Dog6 | Mean | SD |
| 0 | 0 | 0 | 0 | 0 | 0 | 0 | 0 | 0 |
| 0.083 | 1850 | 4530 | 1190 | 521 | 2070 | 2290 | 2075 | 1365 |
| 0.25 | 9040 | 19600 | 7610 | 9590 | 2810 | 12100 | 10125 | 5567 |
| 0.5 | 10200 | 28600 | 13800 | 16600 | 12400 | 15000 | 16100 | 6504 |
| 1 | 13300 | 24100 | 16600 | 21900 | 21700 | 18200 | 19300 | 4001 |
| 1.5 | 18000 | 23900 | 16900 | 20900 | 23100 | 16900 | 19950 | 3125 |

TABLE 14-continued

Plasma concentration of Group 1

| Time (h) | Plasma concentration of Ibuprofen (ng/mL) | | | | | | | |
|---|---|---|---|---|---|---|---|---|
| | Dog1 | Dog2 | Dog3 | Dog4 | Dog5 | Dog6 | Mean | SD |
| 2 | 16300 | 23600 | 14400 | 21500 | 21300 | 18800 | 19317 | 3481 |
| 3 | 14100 | 20900 | 12600 | 21300 | 17500 | 19900 | 17717 | 3662 |
| 4 | 10300 | 16700 | 12200 | 17400 | 14900 | 14800 | 14383 | 2696 |
| 6 | 6340 | 9630 | 5560 | 10800 | 5990 | 9390 | 7952 | 2243 |
| 8 | 3440 | 4730 | 2440 | 5830 | 2020 | 5620 | 4013 | 1623 |
| 24 | 184 | 88.9 | 59.7 | 409 | 154 | 180 | 179 | 123 |

TABLE 15

Plasma concentration of Group 2

| Time (h) | Plasma concentration of Ibuprofen (ng/mL) | | | | | | | |
|---|---|---|---|---|---|---|---|---|
| | Dog1 | Dog2 | Dog3 | Dog4 | Dog5 | Dog6 | Mean | SD |
| 0 | 0 | 0 | 0 | 0 | 0 | 0 | 0 | 0 |
| 0.25 | 0 | 98.9 | 126 | 49.1 | 189 | 277 | 123 | 99 |
| 0.5 | 504 | 31200 | 1950 | 110 | 450 | 1650 | 5977 | 12378 |
| 1 | 6880 | 28000 | 21600 | 1050 | 1000 | 3030 | 10260 | 11641 |
| 1.5 | 21400 | 24800 | 20300 | 6160 | 11600 | 4280 | 14757 | 8595 |
| 2 | 20500 | 24800 | 15300 | 6600 | 11500 | 5310 | 14002 | 7709 |
| 3 | 14500 | 16100 | 8520 | 18400 | 8740 | 20600 | 14477 | 4978 |
| 4 | 9540 | 11800 | 4030 | 15400 | 5620 | 14300 | 10115 | 4601 |
| 6 | 6200 | 6370 | 2280 | 8450 | 4310 | 8990 | 6100 | 2520 |
| 8 | 2970 | 3750 | 1060 | 3420 | 2840 | 3920 | 2993 | 1037 |
| 24 | 90.2 | 45.1 | 116 | 260 | 97.9 | 193 | 134 | 78 |

The foregoing examples illustrate the high loading and fast absorption capability of the film of the present film forming composition and use of the film to orally deliver active ingredient. While the foregoing invention has been described with respect to various embodiments and examples, it is understood that other embodiments are within the scope of the present invention as expressed in the following claims and their equivalents. Moreover, the above specific examples are to be construed as merely illustrative, and not limitative of the reminder of the disclosure in any way whatsoever. Without further elaboration, it is believed that one skilled in the art can, based on the description herein, utilize the present invention to its fullest extent. All publications recited herein are hereby incorporated by reference in their entirety.

The invention claimed is:

1. A film forming composition comprising a film forming component and a solvent, wherein the film forming component comprises 30-35% by weight of a first water soluble polymer, 0.5-1% by weight of a second water soluble polymer, 2.4-5.2% by weight of plasticizer and 50%-70% by weight of metoprolol tartrate, the weight ratio of the film forming component to the solvent is 1:0.5-3 and wherein the film forming component has a Tg of 20° C. −30° C.,
   wherein the first water soluble polymer is pullulan with a Tg of greater than 150° C., and the second water soluble polymer is PEO 200K with a Tg of −52° C., and a ratio of the first water soluble polymer to the second water soluble polymer is 34-35:1,
   wherein the film forming component further comprises a filler, and at least one of disintegrating agent, sweetener, surfactant and antifoaming agent,
   wherein the filler is silk fibroin, and
   wherein a resulting film has a dry thickness in approximately 30-35% of a wet thickness thereof.

2. The film forming composition of claim 1, wherein difference of Tg values of the first and second water soluble polymer is 62-268° C.

3. The film forming composition of claim 1, wherein the active ingredient is water soluble.

4. The film forming composition of claim 1, wherein the active ingredient is water insoluble.

5. The film forming composition of claim 4, wherein the active ingredient has a melting point of below 100° C.

6. The film forming composition of claim 3, wherein the active ingredient has a water solubility of at least 100 mM.

7. The film forming composition of claim 1, wherein film forming component comprises 10-40% by weight of a first water soluble polymer, 0.3-10% by weight of a second water soluble polymer and 2.4-10% by weight of plasticizer.

8. The film forming composition of claim 1, wherein the plasticizer is selected from dextran, glycerol, PEG400 and sorbitol.

9. A film formed by the film forming composition of claim 1, wherein the film has a dry thickness of at least 260 μm, a solvent of 7-15% by weight, a disintegrating time of 10-60 sec and active ingredient at 1-40 mg/cm$^2$.

10. The film of claim 9, wherein the film has a dry thickness of at least 300 μm, a solvent of 7-9%, the disintegrating time of 40-60 sec and active ingredient at 6-23 mg/cm$^2$.

11. The film of claim 9, wherein the film is a porous structure.

12. The film of claim 9, wherein the film has a tensile strength of 1.1 kPa.

13. The film of claim 9, wherein the active ingredient reaches 100% dissolution within 300 sec.

* * * * *